(12) United States Patent  (10) Patent No.: US 7,926,325 B2
Kaplit  (45) Date of Patent: Apr. 19, 2011

(54) DIFFERENTIATING BETWEEN ABNORMAL SAMPLE VISCOSITIES AND PIPETTE CLOGGING DURING ASPIRATION

(75) Inventor: Michael Kaplit, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 394 days.

(21) Appl. No.: 12/108,257

(22) Filed: Apr. 23, 2008

(65) Prior Publication Data

US 2009/0266149 A1 Oct. 29, 2009

(51) Int. Cl.
G01N 1/00 (2006.01)
G01N 35/00 (2006.01)
G01B 13/00 (2006.01)

(52) U.S. Cl. .................. 73/37; 73/1.74; 702/50
(58) Field of Classification Search .............. 604/123; 73/37, 1.74; 702/50
See application file for complete search history.

(56) References Cited

U.S. PATENT DOCUMENTS

| | | |
|---|---|---|
| 5,451,373 A | 9/1995 | Lewis et al. |
| 5,463,895 A | 11/1995 | Brentz |
| 5,503,036 A | 4/1996 | Nguyen et al. |
| 5,540,081 A | 7/1996 | Takeda et al. |
| 5,622,869 A | 4/1997 | Lewis et al. |
| 5,814,275 A | 9/1998 | Lewis et al. |
| 5,845,423 A | 12/1998 | Hicks |
| 5,915,282 A | 6/1999 | Merriam et al. |
| 6,022,747 A | 2/2000 | Gherson et al. |
| 6,060,320 A | 5/2000 | Dorenkott et al. |
| 6,283,719 B1 | 9/2001 | Frantz et al. |
| 6,370,942 B1 * | 4/2002 | Dunfee et al. .............. 73/37 |
| 6,432,657 B1 | 8/2002 | Kikuchi et al. |
| 6,472,161 B1 | 10/2002 | Baugh |
| 6,589,791 B1 | 7/2003 | LaBudde et al. |
| 6,938,504 B2 | 9/2005 | Camenisch |
| 7,027,935 B2 | 4/2006 | Shimase et al. |
| 7,634,367 B1 * | 12/2009 | Ding et al. ................ 702/50 |
| 7,694,591 B2 * | 4/2010 | Leibfried ............. 73/864.01 |
| 2004/0020938 A1 | 2/2004 | Boillat et al. |
| 2007/0025882 A1 | 2/2007 | Zuppiger et al. |
| 2007/0143063 A1 | 6/2007 | Kaplit |
| 2009/0070049 A1 * | 3/2009 | Ziegler et al. ............ 702/50 |

* cited by examiner

Primary Examiner — Lisa M Caputo
Assistant Examiner — Punam Roy
(74) Attorney, Agent, or Firm — Leland K. Jordan

(57) ABSTRACT

A method for differentiating between a liquid sample having clogs therein and a liquid sample having an abnormally elevated viscosity during a liquid aspiration process by relating the ratio between the maximum negative pressure during aspiration and an equilibrium pressure prior to dispensation to viscosity.

1 Claim, 7 Drawing Sheets

DIFFERENTIATING BETWEEN ABNORMAL SAMPLE VISCOSITIES AND PIPETTE CLOGGING DURING ASPIRATION

FIELD OF THE INVENTION

The present invention relates to the aspiration of an amount of liquid from a container, and more particularly, to an improved method for differentiating between a clogged liquid sample and a sample having an abnormally elevated viscosity during a liquid aspiration process.

BACKGROUND OF THE INVENTION

Fully automated diagnostic analyzers are commercially available to perform chemical assays and immunoassays of biological liquids such as urine, blood serum, plasma, cerebrospinal liquids and the like. Generally, reactions between an analyte in a patient sample and reagents used during the assay generate a signal from which the concentration of analyte in the patient sample may be calculated. Such automated analyzers generally use an aspirating means such as a sampling tip, or probe or needle, to transfer desired volumes of liquid samples or liquid reagents between receptacles, such as between sample containers, reagent containers and reaction cuvettes disposed on the analyzer. Hereinafter, variations of the term aspirate refer to all of such processes for extracting liquid from one container and depositing at least some of the liquid into the same or another container and further includes the supporting devices required to complete the liquid handling operations.

Aspirators typically comprise an elongated, needle-like probe or pipette having a hollow passage whereby liquid may be aspirated into and/or dispensed from the probe using appropriate pumping resources. The pipette may be carried by a transport mechanism adapted to provide horizontal and vertical movement so as to enable the pipette tip to be lowered into a liquid in a reservoir for aspiration of the liquid, and for transporting the liquid to a another location whereat the pipette is lowered to an optimal position for dispensing the liquid. Some type of device, such as a piston assembly, which may be incorporated into the pipette, is operated electronically to aspirate liquid into the pipette and to dispense liquid from the pipette using vacuum pressures.

It is desirable, when aspirating a liquid, to accurately determine if any abnormalities or non-uniformities within the liquid have adversely affected the overall quality of the aspiration process. Non-uniformities such as clogs, clogs, bubbles, abnormal liquid viscosity, insufficient volume, etc, may exist in liquids, particularly when the liquid is one of several body liquids being analyzed as these frequently are of a non-uniform composition. As used herein, the term "clot" is associated with a physical aggregate in an aspirated liquid while a "clog" is associated with any physical impediment to a successful liquid aspiration other than insufficient sample. Various methods have been developed to detect the effect of such non-uniformities on the aspiration process.

U.S. Pat. No. 6,370,942, assigned to the assignee of the present application and incorporated herein by reference, discloses an method for evaluating the quality of a liquid aspiration for undesirable events such as partial or complete clogs, or aspiration of air by employing three separate aspiration tests including a pressure difference test to verify liquid was aspirated, a pressure recovery test to check for clogs and aspiration of unwanted cells, and a pressure shape test to check for abnormalities during aspiration, such as clogs, air aspiration, density changes (due to aspiration of blood cells), etc.

U.S. Pat. No. 6,022,747 discloses a blood clog detector having a pressure transducer on an aspiration line to provide output voltage data to a microprocessor corresponding to the vacuum level during aspiration. The microprocessor integrates the vacuum readings over time during the aspiration cycle to provide a pressure integral for each test sample aspiration. Acceptability of the test sample for analysis is based upon a predetermined difference between the reference pressure integral and each test sample pressure integral.

U.S. Pat. No. 5,540,081 relates to a pipetting apparatus provided with a pressure sensor and a plurality of pressure difference calculating circuits obtain a pressure difference at a different pressure calculation period. An alarm circuit is included for outputting a clog detection alarm signal when at least one of said discriminating circuits discriminates that the obtained pressure difference exceeds the discrimination threshold value.

U.S. Pat. No. 5,503,036 relates to an obstruction detection circuit for detecting an obstruction of a sample probe of an automated liquid sample aspiration/dispensation device. Pressure within a connecting conduit is measured shortly after the start of the aspiration or dispensation of a sample and again measured after the completion of the aspiration or the dispensation by the pump. If the pressure has not returned to a predetermined range within a predetermined amount of time, an error condition is reported.

U.S. Pat. No. 5,463,895 discloses provides an apparatus and method of detecting non-homogeneity in a liquid sample, such as the presence of foam or bubbles on the surface of the sample, and/or the presence of clogs on the surface or in the bulk of the sample. This method involves determining the ambient air pressure within a pipettor, aspirating air into the pipettor as the pipettor moves towards a sample in container and monitoring for a pressure change in the pipettor to indicate the surface level of the liquid in said container. Pressure changes are monitored after aspiration and compared to predetermined normal aspiration pressure windows.

U.S. published patent application 20070143063, assigned to the assignee of the present application and incorporated herein by reference, discloses a method for verifying the integrity of an aspiration process by determining the profile of an entire aspiration pressure curve and then determining by numerical analysis whether the difference between the actual and the mathematical approximation to a portion of the profile is less than the standard deviation of the residuals of a linear regression analysis of an aspiration pressure curve measured on a sample known to have clogs therein or known to be less than a desired aspiration volume.

As the state of the art in clinical analysis advances, aspirated sample volumes are increasingly smaller, causing pressure differential values for liquids with different viscosities to become more erratic or "noisy". In addition, pressure profiles of higher viscosity liquids do not reach stable end-point values. Hence, there is a need for a method for differentiating between a clogged liquid sample and a sample having an abnormally elevated viscosity during a liquid aspiration process.

SUMMARY OF THE INVENTION

It is therefore an object of this invention to provide a method for differentiating between a clogged liquid sample and a sample having an abnormally elevated viscosity during a liquid aspiration process. This is accomplished by first confirming from analysis of the aspiration pressure (vacuum) profile that a minimum sample volume exists. Next, the standard deviation of the residuals is measured from a linear regression analysis of the aspiration pressure profile over a shortened final portion of the aspiration pressure profile. If the standard deviation of the residuals is greater than a predetermined critical value, then the aspiration process may have failed due to a leak, a faulty pump, etc., or may have been conducted on a sample that has insufficient volume, clogs, foaming, bubbles, or an abnormally elevated viscosity. To differentiate between a clogged sample and a high-viscosity sample, the ratio between the maximum negative pressure during aspiration and an equilibrium pressure prior to dispensation is calculated. It has been discovered that this ratio is unexpectedly linearly related to the viscosity of aspirated liquid and can therefore be used to differentiate between a clogged liquid sample and a sample having an abnormally elevated viscosity.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
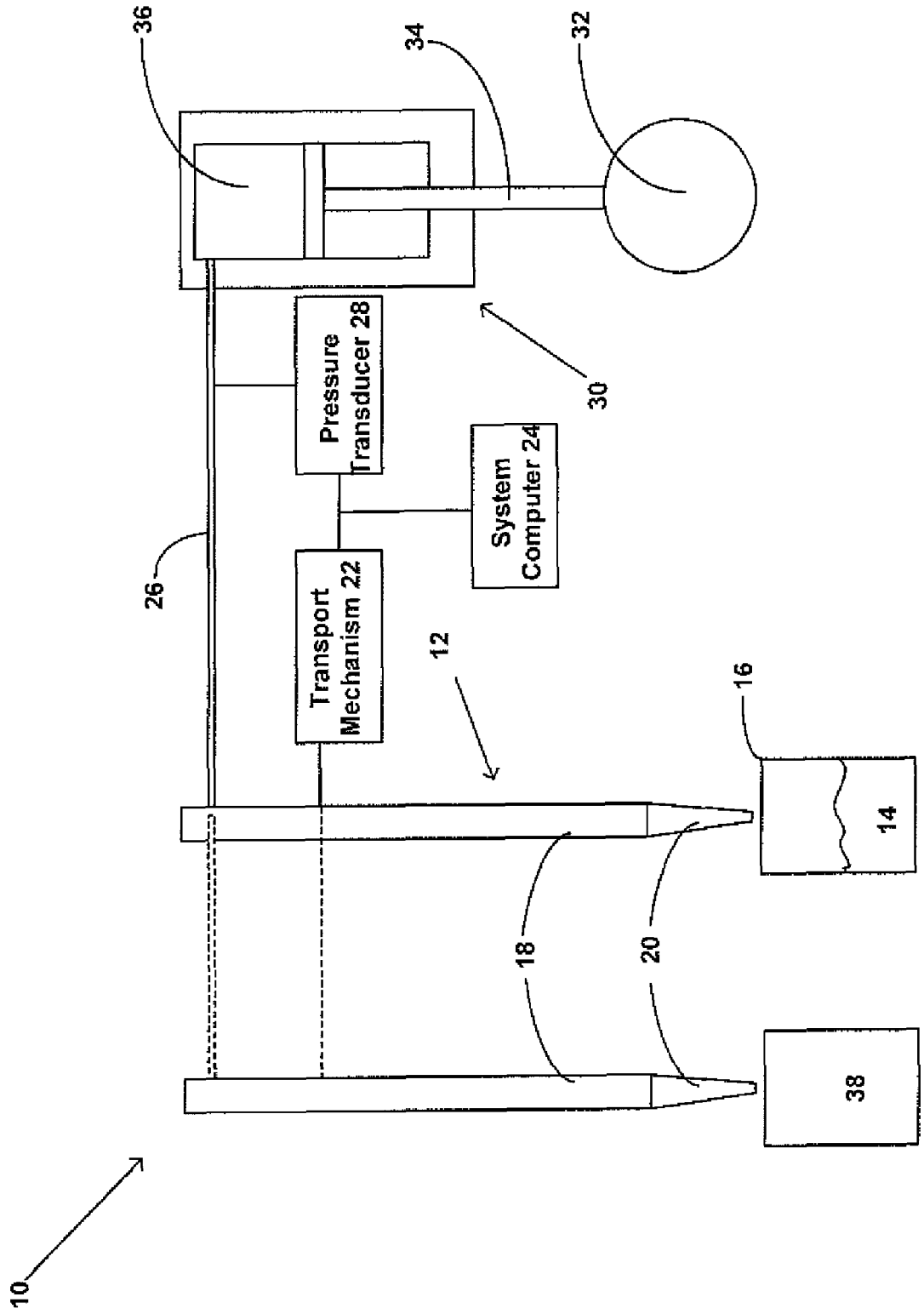
FIG. 1 is a schematic representation of an aspiration system in which the present invention may be practiced.

FIG. 1 illustrates a liquid aspirating and dispensing system 10 useful in practicing the present invention which includes a pipette 12 for aspirating and dispensing liquid such as a sample liquid 14 contained in a container 16, like described in co-pending U.S. patent application Ser. No. 11/857,922 assigned to the assignee of the present application and incorporated herein by reference. Although one such sample liquid 14 is shown for the purpose of describing the liquid dispensing system 10, it will be apparent to those skilled in the art that any number of sample liquid containers 16 can be present in an automated clinical analyzer like described in co-pending U.S. patent application Ser. No. 11/941,204 assigned to the assignee of the present application and incorporated herein by reference, including patents and patent applications incorporated therein by reference and like described in co-pending U.S. patent application Ser. No. 10/862,507 assigned to the assignee of the present application and incorporated herein by reference, including patents and patent applications incorporated therein by reference. In an exemplary embodiment, the liquid aspirating and dispensing system 10 may be used in an automated clinical analyzer (not shown). Such automated clinical analyzers are known in the art and those skilled in the art will know with certainty the functions of the elements of the analyzers to which reference is made.

Pipette 12 generally includes a central cavity 18 which may be adapted to carry a replaceable pipette tip 20 which may have a conically narrowing nose shape terminating in a distal orifice 40 through which liquid is aspirated into cavity 18, and through which liquid is dispensed therefrom. Central cavity 18 opens into the tip cavity upon engagement of the holder with the tip. Alternately, pipette tip 20 may be integral with central cavity 18. Liquid aspirating and dispensing system 10 further comprises an aspirating/dispensing pressure control 30 adapted to produce a vacuum pressure within cavity 18 during aspiration and a positive pressure during dispensing. Pressure source 30 is connected to pipette by tubing 26 and the pressure therein is monitored with a pressure transducer 28 interfaced to a system computer-based controller 24 programmed to practice the present invention as well as to control the operation of an analytical analyzer associated therewith. Typical of pressure source 30 is a piston assembly 32 connected with tubing 26 and the pipette 12 on a top side thereof, opposite pipette tip 20. Aspiration systems 10 like seen in FIG. 1 are well known to those skilled in the art and may be implemented with a variety of components and designs. To practice the present invention requires only that vacuum pressure be used to aspirate and dispense from pipette 12 and that the aspirating and dispensing pressure be monitored.

Liquid aspirating and dispensing system 10 typically includes a transport device 22, indicated diagrammatically, which may be of any suitable type. The transport device 22 is capable of moving the pipette 12 laterally (the X-direction), vertically (the Z-direction) and from front to back (the Y-direction) in an analyzer to enable the pipette 12 to pick up a pipette tip 20 (when disposable tips are used), aspirate liquid 14 into the pipette tip 20 from a sample liquid reservoir 16 or tube 16 and to dispense a desired amount of sample liquid into an assay cuvette 38. Generally, stepper-motors, electronic drivers, interface circuits and limit-switches are used within transport device 22 to control transporting the pipette 12 and these are interfaced to system computer 24.

As shown, pipette 12 has a cavity 18 for holding liquid 14 and a tube 26 connected therefrom to a vacuum pressure measurement device or transducer 28 and to pressure control 30 for producing a variable vacuum pressure throughout the pipette 12 responsive to commands from computer 24. Pipettes 12 may be made from metals like stainless steel or plastics like polypropylene and similar materials, and tubing 26 made from vinyl, polypropylene, polyethylene, metal, etc, may used in the present invention. Pressure measurement device 28 measures air pressure within the pipette 12 both continuously and periodically during the aspiration method of the present invention. An exemplary pressure measurement device 28 is a pressure transducer (Model SCXL004DN from SenSym, Miltipas, Calif.) interfaced to the computer 24 to provide a measured air pressure within tubing 26 to computer 24.

An exemplary aspiration pressure control 30 is a piston-syringe device, mechanically connected to a stepper motor 34 and encoders or home limit-switches (not shown) capable of controlling the movement of the syringe piston and causing pressure control 30 to aspirate and dispense air through tubing 26. Aspiration pressure control 30 and pressure sense device 28 are electronically interfaced to computer 24 which is used to control the operation of the liquid aspiration system 10. The computer 24 also provides signals to control the movement of the pipette 12 via transport device 22 as well as the aspiration into, and dispensing of liquid from, the pipette tip 24.

In such an instance, as illustrated in FIG. 1, pressure control 30 comprises a piston 34 attached to motor 32 for advancing and retracting the piston 34 within a closed chamber 36. A downward movement of piston 34 tends to increase the volume of the chamber 36, thereby to create vacuum or negative air pressure within the chamber 36 which draws air from the interconnected tubing 26, cavity 18, and pipette tip 20 into cavity 18 for aspirating liquid 14 into pipette tip 20. Advancing piston 36 into chamber 36 decreases the volume of chamber 36, thereby to provide a positive air pressure which pushes air out of chamber 36 into the interconnected tubing 26, cavity 18, and pipette tip 20 for expelling and dispensing liquid from the pipette tip 20 via the tip orifice into assay cuvette 38. For purposes of simplicity, FIG. 1, shows transport device 22 and tubing 26 in dotted lines when pipette 12 is placed over assay cuvette 38 and previously aspirated liquid 14 is dispensed into assay cuvette 38. The piston 36 provides for aspiration of liquid 14 into pipette 12 and dispensing of liquid 14 from pipette 12 into assay cuvette 38.

In practicing the present invention, aspiration pressure control 30 and pressure sense device 28 are controlled and analyzed by computer 24 so as to determine the viscosity of the aspirated sample liquid 14 through analysis of a pressure profile generated during the aspirating and dispensing processes. Viscosity of aspirated sample liquid 14 is determined by means of a series of mathematical analyses, as follows and as explained hereinafter in greater detail.

Pressure data, for instance using an A/D (analog signals converted to digital data) converter, are collected in real time during the aspirating and dispensing cycle. In a typical embodiment, an analog input subsystem reads the pressure sense device at a constant rate (for example, at 500 Hz) time stamping each reading and buffering the reading(s) for eventual inclusion into the aspiration data set. In parallel to the aspiration process, the pressure data are periodically transferred from the analog sub-system buffer into the aspiration data set. The aspiration data set consists of a series of time stamped pressure readings that occur before and during the initial portion of pump operation. Each process event (start of aspiration cycle, start of pump cycle, end of aspiration pressure readings) is marked in the data set. To achieve close coupling with process event, the data are also read from the analog sub-system coincident with these events. The resultant aspiration data set then contains a multiple of time stamped pressure and event markers that allow analysis of the aspirating and dispensing processes.

Sensing of the upper surface portion of the sample liquid 14 may be performed via system 10 using capacitive level sensing techniques known in the art and like that described in U.S. Pat. No. 7,150,190 assigned to the assignee of the present application and incorporated herein by reference. The technique disclosed therein confirms that a change in capacitance within a liquid level sensor is caused only by true physical contact between a probe and a liquid by verifying that any change in capacitance of the liquid level sensor is repeatable and constant over a given time period and thereby is caused by actual contact the probe and liquid and is not caused by spurious electrical disturbances or other measuring irregularities.

Once liquid level in the reservoir 16 has been determined, sample aspiration commences. A vacuum generated by the aspiration pressure control 30 draws sample liquid 14 up into the pipette tip 20. At the sample time, pipette 12 descends to follow the level of the sample down in reservoir 16, keeping the tip 20 immersed in liquid 14. Different descent rates are used, depending on the diameter of the reservoir 16. After aspiration is completed, the pressure profile is examined as described hereinafter and pipette tip 20 is retracted from liquid sample 14. Finally, a quantity of aspirated sample liquid 14 is dispensed into cuvette 38 by decreasing vacuum pressure using aspiration pressure control 30.

Figure 2:
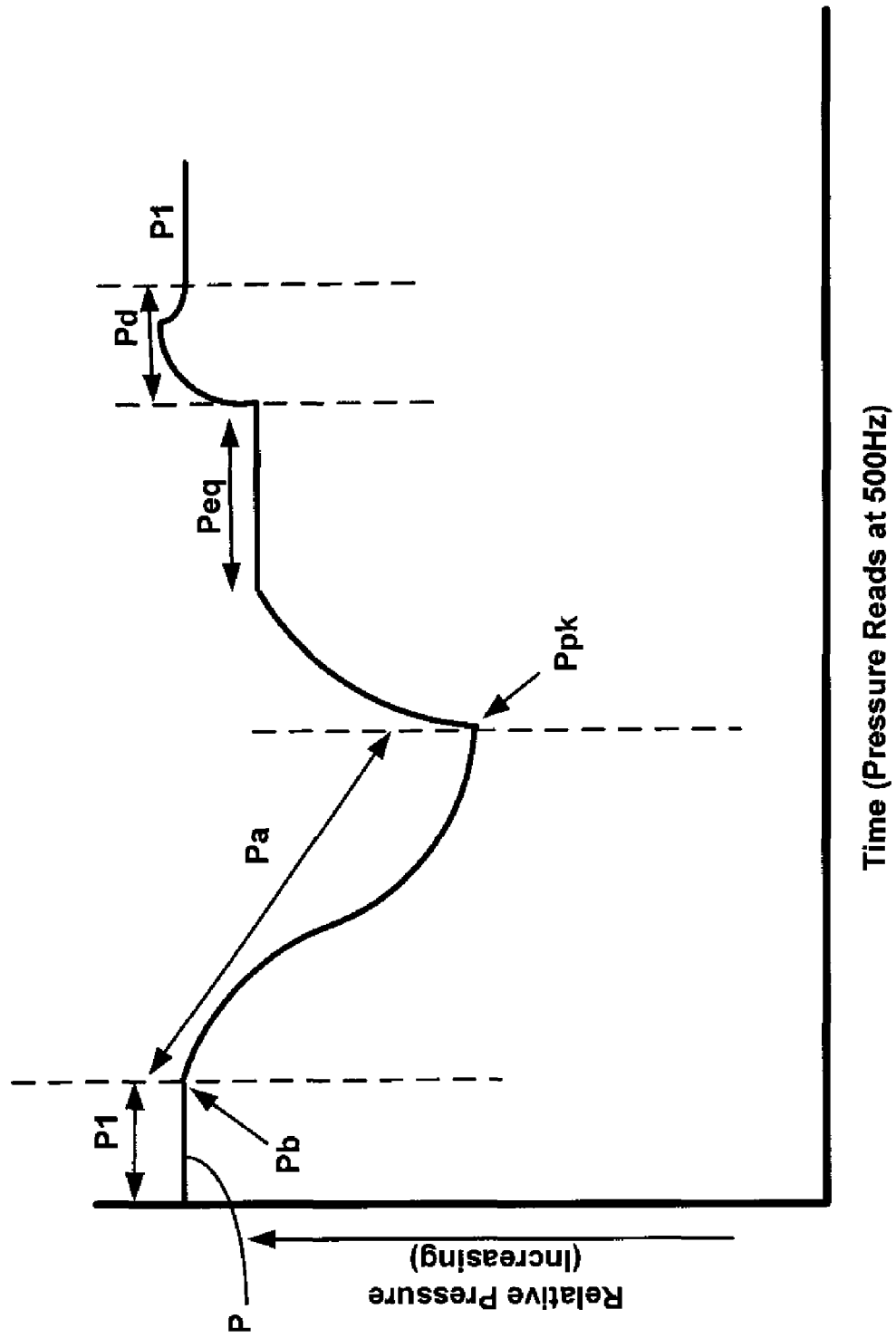
FIG. 2 is a graphical representation of a typical aspiration pressure profile obtainable with the aspiration system of FIG. 1 illustrating a clog free sample of sufficient volume and normal viscosity to enable a successful sample aspiration.

FIG. 2 is illustrative of the well-known aspiration pressure profile is a graphical representation of a typical aspiration pressure profile obtainable with the aspiration system of FIG. 1 illustrating a clog-free sample of sufficient volume and normal viscosity to enable a successful sample aspiration. As used herein, the terms "normal" and "elevated" as applied to sample viscosity are generally understood to have their usual meaning as applied to liquids found in patient sample, wherein "normal" implies a viscosity in the range of 2-12 centipoises and "abnormal or elevated" implies a viscosity grater than about 15 centipoises. In addition, the term "clog" as used herein refers to any physical impediment to a successful sample aspiration other than insufficient sample volume and the term "clog" refers to a physical aggregate within the sample liquid that prevents a successful sample aspiration, normally as a consequence of partially or fully blocking pipette tip 20.

The aspiration process of FIG. 2 includes the following events:

$P1$=baseline pressure prior to aspiration of liquid 14 into pipette 12

$Pb$=relative pressure at beginning of aspiration of liquid 14 into pipette 12

$Pa$=relative pressure measurement range during actual aspiration $Ppk$=peak pressure during aspiration of liquid into pipette 12

$Peq$=relative pressure at equilibrium after aspiration and prior to dispensing $Pd$=relative pressure during dispensing of liquid into cuvette 38

One of the parameters known to affect an aspiration process is the desired volume of aspirated liquid 14. Computer 24 is programmed, among other operations, to control the operation of the liquid aspiration system 10 to deliver such a desired volume, in particular by operating aspiration pressure control 30 for a predetermined length of time after Pb is established. This is the period of time, the "aspirating and dispensing cycle time" during which pressure measurements are made during aspiration of liquid into pipette 12 and during dispensing of liquid into cuvette 38, ending at a point in time at which P, the pressure prior to aspiration of liquid 14, is re-achieved.

As explained in greater detail hereinafter, the present invention monitors the aspirating and dispensing process to determine viscosity of aspirated liquid and/or the presence of clogs therein, by first analyzing the aspiration pressure (vacuum) profile to confirm that sufficient sample liquid 14 has been aspirated into pipette 12. Next, the standard deviation of the residuals is measured from a linear regression analysis of the aspiration pressure profile over a shortened final portion of the aspiration pressure profile. If the standard deviation of the residuals is greater than a predetermined critical value, then it is determined that sample liquid 14 is either clogged or has abnormally elevated viscosity. To differentiate between a clogged sample and a high-viscosity sample, the ratio between the maximum negative pressure during aspiration and an equilibrium pressure prior to dispensation is calculated. Finally, this ratio is used to ascertain if the viscosity of aspirated liquid is within normal limits and therefore used to differentiate between a clogged liquid sample and a sample having an abnormally elevated viscosity.

The first step in the instant process for confirming that the pipette tip 20 is not blocked by a clog and that the viscosity of liquid 14 is within a normal range is achieved by calculating the Peak Pressure Ppk during aspiration, the Peak Pressure Ppk being the absolute magnitude of the Pressure Peak minus the baseline pressure P. The Pressure Peak Ppk is the maximum negative pressure experienced during aspirating and occurs at about the time after Pb when the aspirating/dispensing pressure control 30 ceases to increase vacuum pressure after aspirating the desired liquid volume. In the embodiment illustrated in FIG. 1, piston assembly 32 ceases movement. The baseline pressure P is an averaged pressure reading obtained immediately before an empty pipette 12 is inserted into liquid 14. By itself, the Peak Pressure Ppk cannot accurately differentiate between a clogging of the pipette tip 20 and a sample liquid 14 having too high a viscosity.

Figure 6:
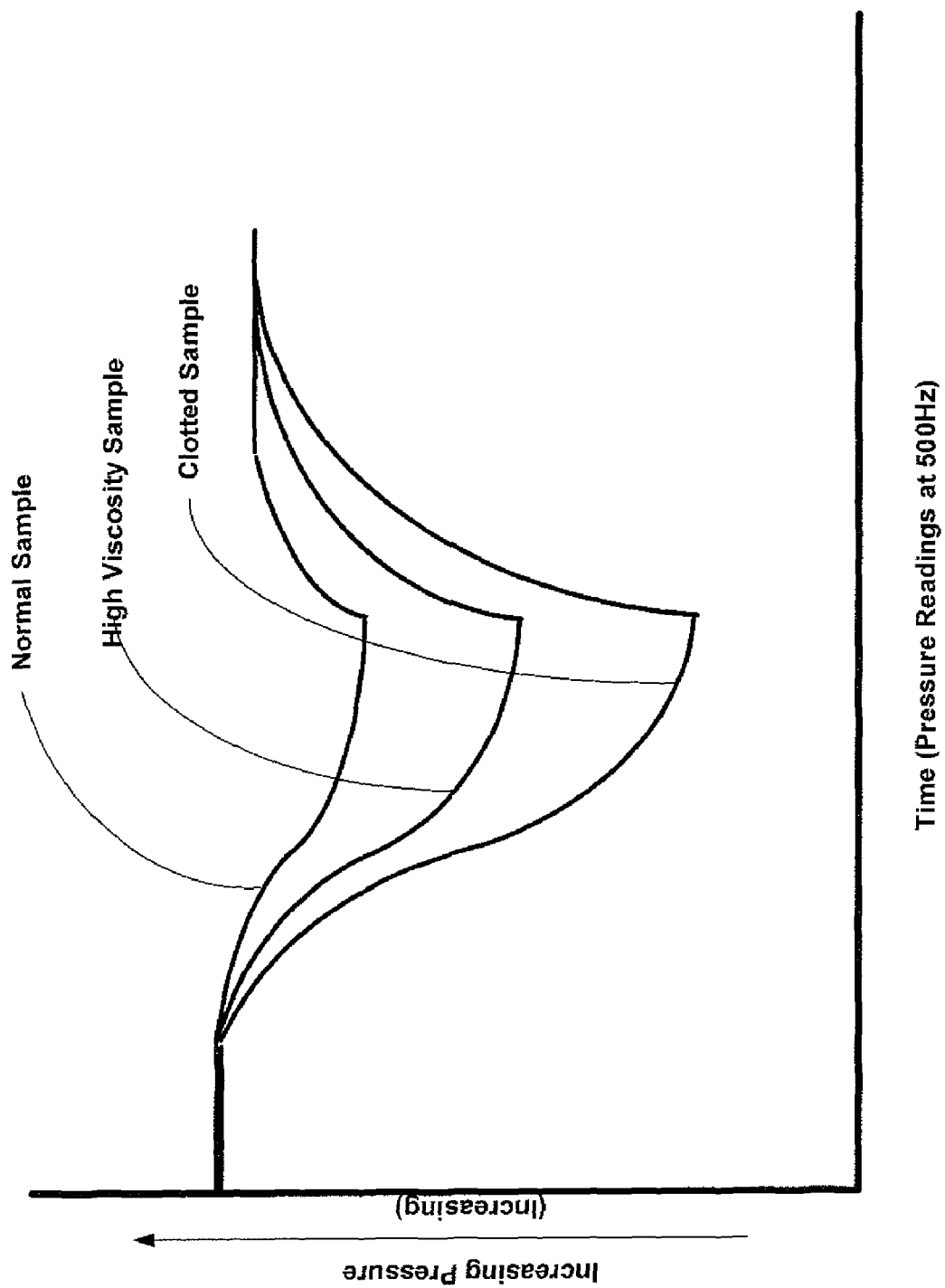
FIG. 6 is a graphical representation of a typical aspiration pressure profile obtainable with the aspiration system of FIG. 1 illustrating the pressure profiles of 200 ul aspirates of 2 clog free water samples, a high viscosity sample, and a water sample with a wetted paper ball simulating a sample having a clog; and, FIG. 7 is a graphical representation of a typical aspiration pressure profile obtainable with the aspiration system of FIG. 1 illustrating aspiration of a sample having less than a desired volume.

As may be seen in FIG. 6, the pressure profile in the vicinity of the Peak Pressure Ppk has a similar profile regardless of whether the sample liquid is of a low water-like viscosity or of a much higher glycerol-like viscosity, typically 18.5 cp, or is a low water-like viscosity sample liquid having a wetted paper ball therein to simulate a clog. An empirically determined upper limit for the Peak Pressure Ppk may only be used to determine that either the pipette tip 20 has been clogged or that the sample liquid viscosity is greater than a minimum value.

Next, as described in co-pending U.S. patent application Ser. No. 11/311,532 assigned to the assignee of the present application and incorporated herein by reference, the difference between the actually measured aspiration pressure profile and the aspiration pressure profile of a "normal, error free" aspiration at a particular time during aspiration is determined. It has been observed that the measured aspiration pressure profile is generally linear over the time interval Pa. Any deviation from this linearity suggests that there has been an undesirable occurrence during aspiration. One way to quantify deviation from linearity is to fit a linear regression line LRL to the actually measured aspiration pressure values and then calculate the standard deviation of the regression between LRL and the actually measured aspiration pressure values. The standard deviation of the residuals over the aspiration pressure profile thus measures the fit or lack of fit between a profile in the absence of abnormalities or non-uniformities and the measured profile. However, a low standard deviation of the residuals is not by itself an indicator of a successful sample volume aspiration. For example, the standard deviation of the residuals for the simulated clog profile shown schematically in FIG. 7 could be very small, especially if the sample was of insufficient aspiration volume.

The residuals can consist of both random error and systematic error parts referred to as the variance error and the bias error. (N. R. Draper and H. Smith, "Applied Regression Analysis," John Wiley & Sons, 1966, pp. 36 . . . ) For the present invention either error indicates an abnormality or non-uniformity of the aspirated liquid. A high standard deviation of the residuals would suggest that the sample was abnormal or had non-uniformities. There are a number of other well-known mathematical procedures for testing that the standard deviation of the residuals does or does not exceed a given value. (Abraham Wald, "Sequential Analysis," Dover Publications, 1947, pp. 125)

Figure 3:
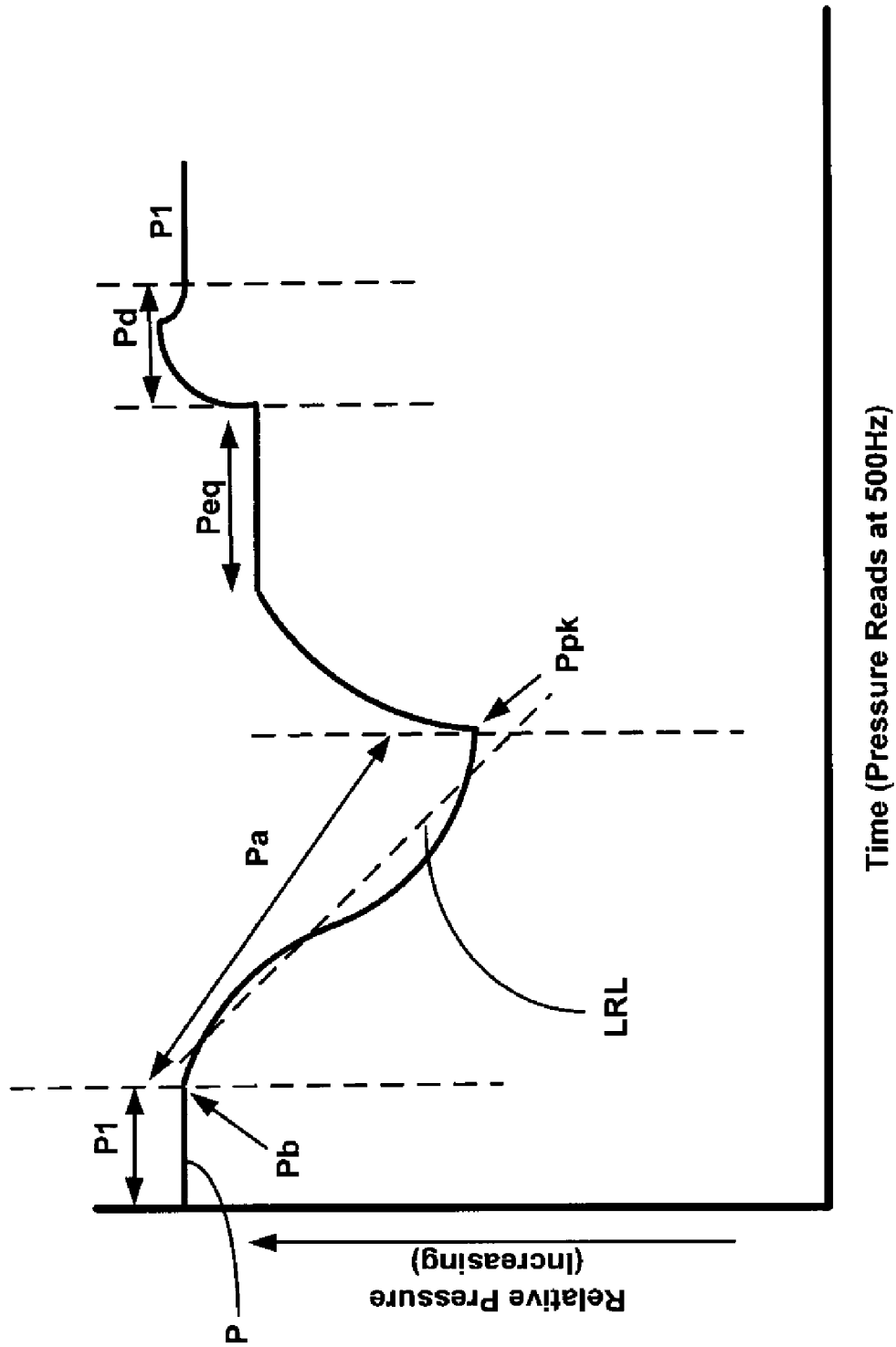
FIG. 3 is the graphical representation of FIG. 3 illustrating a Linear Regression Analysis of a portion of the aspiration pressure profile.

In an illustrative embodiment, like seen in FIG. 3, the residual variance is calculated as a measure of the variation of the actual pressure values measured over the time interval Pa, from a linear regression line LRL, predetermined for a clog-free sample of sufficient volume and normal viscosity to enable a successful sample aspiration. Residual Variance RV is given by the following equation where y is the actual measured pressure value, y' is the pressure calculated by the LRL formula, y−y' is the residual, and n is the number of data points.

$$(RV)^2 = (y-y')2n-2$$

Figure 4:
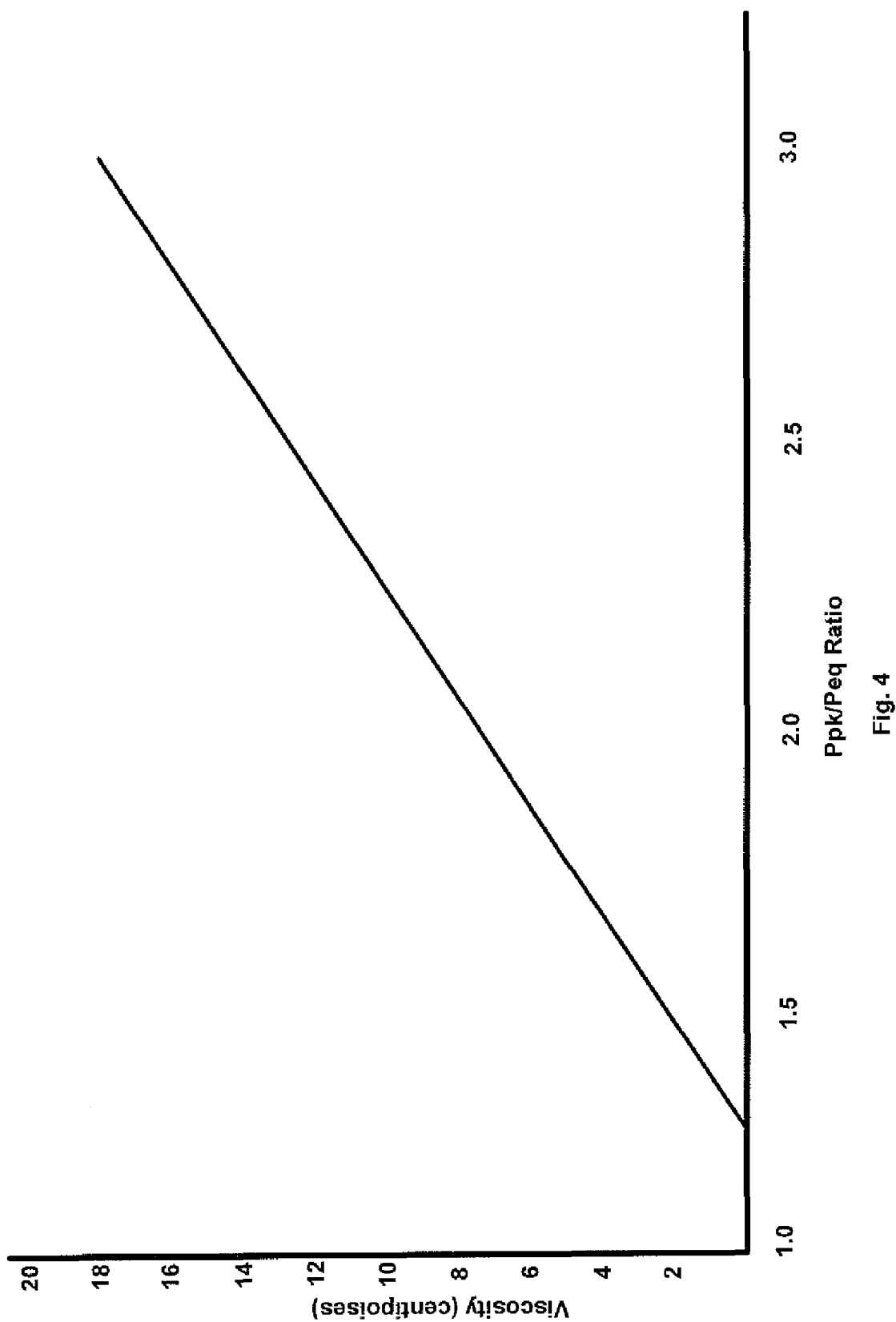
FIG. 4 is a graphical representation of a determined relationship between sample viscosity and pressure ratios determined for the aspiration pressure profile of FIG. 3.
Figure 5:
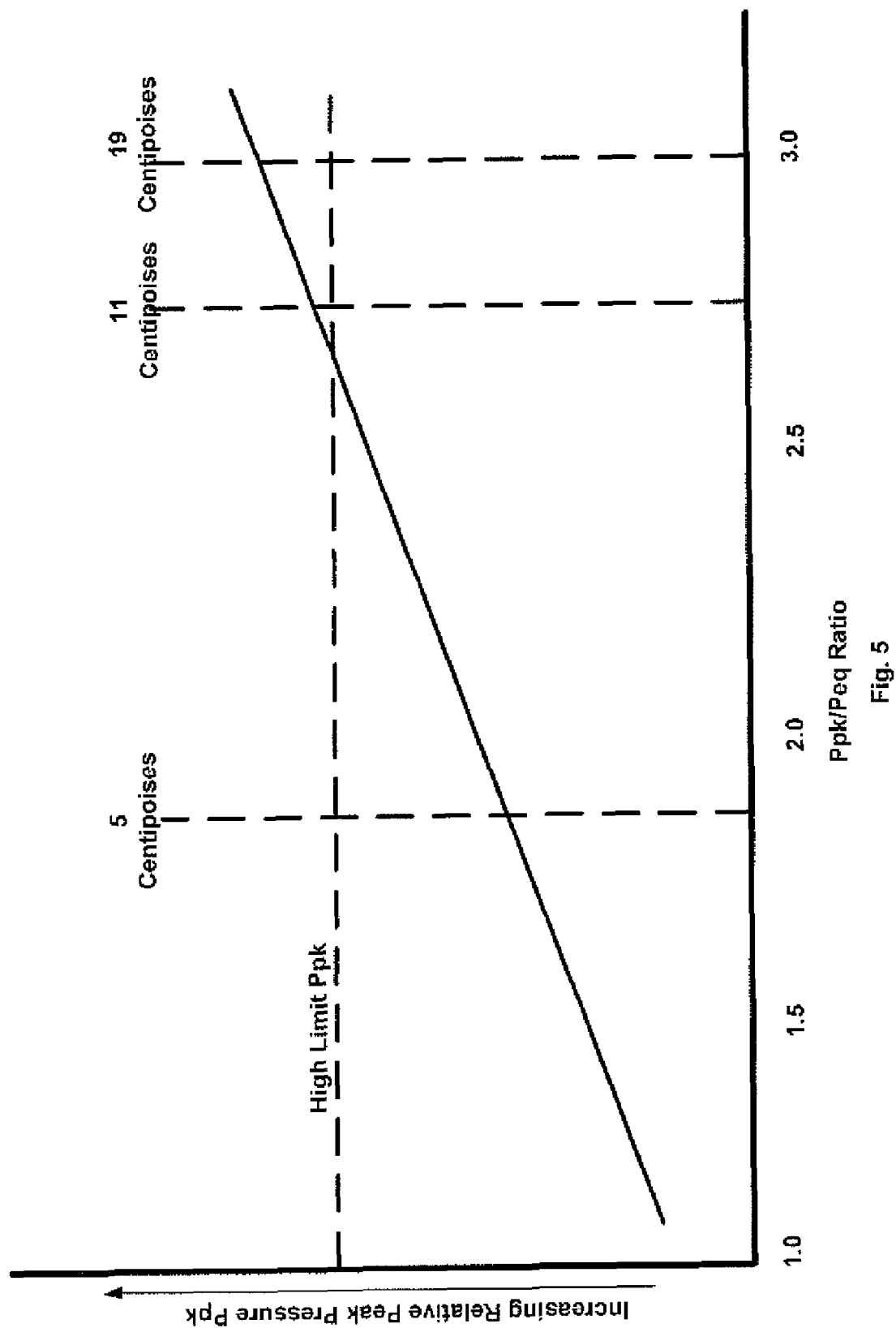
FIG. 5 is a graphical representation of a determined relationship between a Peak Pressure and pressure ratios determined for the aspiration pressure profile of FIG. 3.

It has been discovered that when an aspiration process has been conducted on a "normal sample of sufficient volume and normal viscosity", and satisfies both the Peak Pressure Ppk and Residual Variance requirements, then a newly-defined Peak/Equilibrium Ratio test may be implemented to differentiate between a blockage at the pipette tip 20 and a liquid sample having an abnormally high viscosity. The first step of this Peak/Equilibrium Ratio test is to calculate the ratio of the Peak Pressure Ppk to the relative pressure at equilibrium after aspiration Peq. In an exemplary embodiment, aspiration and dispensing pressure values are measured every 2 ms and Peq can be the average of the last 50 pressure readings immediately before the beginning of Pd minus the baseline pressure. FIG. 4 shows an empirically discovered relationship between the viscosity of liquid samples as a function of Peak/Equilibrium Ratio. Determining whether the Peak Pressure Ppk has exceeded the upper limit of the Pressure Test due to a clog blocking the pipette tip 20 or due to too high a sample viscosity may then be accomplished by first determining sample viscosity from the relationship depicted in FIG. 4. Empirically determined results, like illustrated in FIG. 5 for samples having viscosities of 5, 11 and 19 centipoises predetermine that if the sample viscosity is greater than about 10 centipoises, then the High Limit of the Peak Pressure Ppk, shown as a horizontal dashed line, is exceeded as a result of the sample having too high a viscosity. If the sample viscosity does not exceed 10 centipoises but the Peak Pressure Ppk exceeds the High Limit of the Pressure Test, then, barring an equipment failure, the sample had a clog blocking the pipette tip 20.

This differentiation between an elevated sample viscosity and a clogged sample is most effective when applied after the aspiration process has passed a Delta-Pressure described next and the Residual Variance requirements test, previously described.

Figure 7:
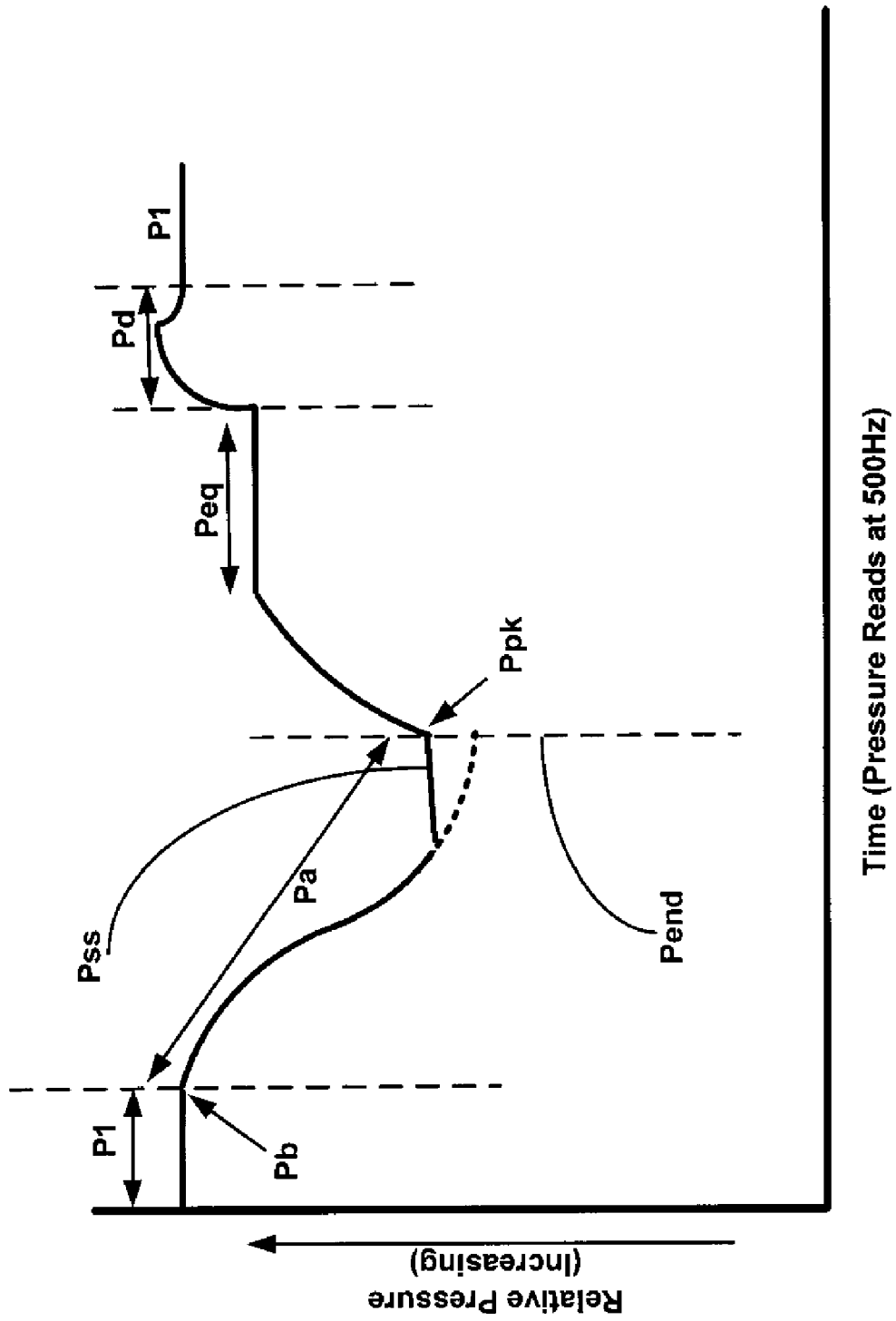

The Delta-Pressure process monitors the aspiration process for the aspiration of air due to a sample being short over a limited portion of the aspiration cycle covering a period of time immediately prior to Pend. FIG. 7 is a graphical representation of an aspiration pressure profile obtainable with the aspiration system of FIG. 1 illustrating sample of insufficient volume to enable a successful sample aspiration in accord with the present invention. The invention is based on the fact that, during the Pend range, if a short sample is encountered, the pressure measured by pressure transducer 28 will level off as indicated by the generally horizontal line identified as "Pss" in FIG. 7. In order to reduce system load on computer 24, the Pend range is generally selected to be in the range of about 20% of the full aspiration cycle that begins with Pb and ends at Pend. The aspiration process is determined to have been conducted on a sample of sufficient volume if, and only if, the difference between Pb and Ppk exceeds a predetermined value. The dashed line in FIG. 7 is indicative of a proper aspiration process and is included to contrast the overall shape of a proper and a short-ample aspiration processes.

Those skilled in the art will appreciate that the embodiments of the invention disclosed herein are illustrative of the principles of the invention and that other modifications may be employed which are still within the scope of the invention. For example, the High Limit Ppk values would be expected to change from those illustrated herein as a result of variations in the diameter of nozzle tip 20 and/or tubing 26, changes in the types of pressure source 30. Accordingly, the present invention is not limited to those embodiments precisely shown and described in the specification but only by the following claims.

The invention claimed is:

1. A method for differentiating between a clogged condition and an elevated viscosity condition of a patient's liquid sample during an aspirating and dispensing process comprising:

determining the profile of a pressure curve representative of said aspirating and dispensing process on said liquid sample;

confirming from said profile that a minimum sample volume of said sample has been aspirated during said aspiration process;

calculating the ratio of a peak pressure value found in an aspirating portion of said profile to an equilibrium pressure value prior to a dispensing portion of said profile;

determining the viscosity of said sample from said ratio; and determining that said sample is not clogged if the viscosity of said sample is less than a predetermined value, or determining that said sample has an elevated viscosity if the viscosity is greater than the predetermined value.

* * * * *